United States Patent
Lee et al.

(10) Patent No.: US 6,193,994 B1
(45) Date of Patent: Feb. 27, 2001

(54) LOCALLY ADMINISTRABLE, BIODEGRADABLE AND SUSTAINED-RELEASE PHARMACEUTICAL COMPOSITION FOR PERIODONTITIS AND PROCESS FOR PREPARATION THEREOF

(75) Inventors: Jae-Yong Lee; Min-Hyo Seo; In-Ja Choi, all of Taejeon-si; Jee-Hyang Kim, Kyungsangbuk-do; Chaul-Min Pai, Taejeon-si, all of (KR)

(73) Assignee: Samyang Corporation (KR)

(*) Notice: Subject to any disclaimer, the term of this patent is extended or adjusted under 35 U.S.C. 154(b) by 0 days.

(21) Appl. No.: 09/180,480

(22) PCT Filed: May 22, 1997

(86) PCT No.: PCT/KR97/00093

§ 371 Date: Mar. 4, 1999

§ 102(e) Date: Mar. 4, 1999

(87) PCT Pub. No.: WO97/44016

PCT Pub. Date: Nov. 27, 1997

(30) Foreign Application Priority Data

May 23, 1996 (KR) .................................................. 96-17798
May 23, 1996 (KR) .................................................. 96-17799

(51) Int. Cl.$^7$ .................................................. A61L 15/28
(52) U.S. Cl. .................. 424/444; 424/426; 424/488; 424/489; 424/490; 424/493; 424/497; 514/953
(58) Field of Search .................. 424/422, 423, 424/424, 425, 426, 443, 444, 484, 488, 489, 490, 493, 497; 514/953, 964, 965

(56) References Cited

U.S. PATENT DOCUMENTS

| | | | |
|---|---|---|---|
| 4,933,182 | * | 6/1990 | Higashi et al. ............ 424/435 |
| 5,185,152 | * | 2/1993 | Peyman .................... 424/427 |
| 5,614,221 | * | 3/1997 | Fjellstrom ................. 424/488 |
| 5,801,116 | * | 9/1998 | Cottrell et al. ............. 502/404 |
| 5,827,937 | * | 10/1998 | Agerup .................. 536/123.12 |
| 5,854,382 | * | 12/1998 | Loomis ..................... 528/354 |

* cited by examiner

Primary Examiner—Robert H. Harrison
(74) Attorney, Agent, or Firm—Bachman & LaPointe, P.C.

(57) ABSTRACT

This invention relates to locally administrable, biodegradable and sustained-release pharmaceutical composition for periodontitis and process for preparation thereof, which can show continuous drug effect for a long time by controlling the release time and by making the drug remain in the periodontal pocket for a prolonged time. The composition is prepared by i) making a microsphere containing the physiologically active substance, ii) making the mixture of the microspheres and water-soluble polymer such as polysaccharides iii) making the mixture into the form of film or strip or/and iv) coating the film or strip with a cation aqueous solution such as calcium and barium.

The present pharmaceutical composition can be easily administered using forceps, has minimized side effects and maximizes the effect by releasing the active substance at the minimum dose, and make the patients feel comfortable.

8 Claims, 5 Drawing Sheets

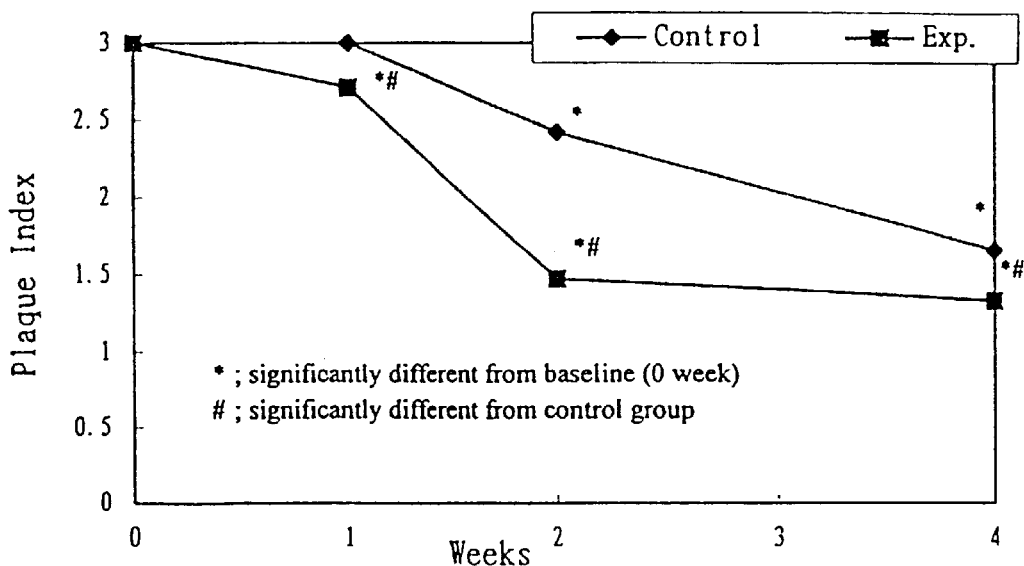
Fig. 1 Plaque Indices
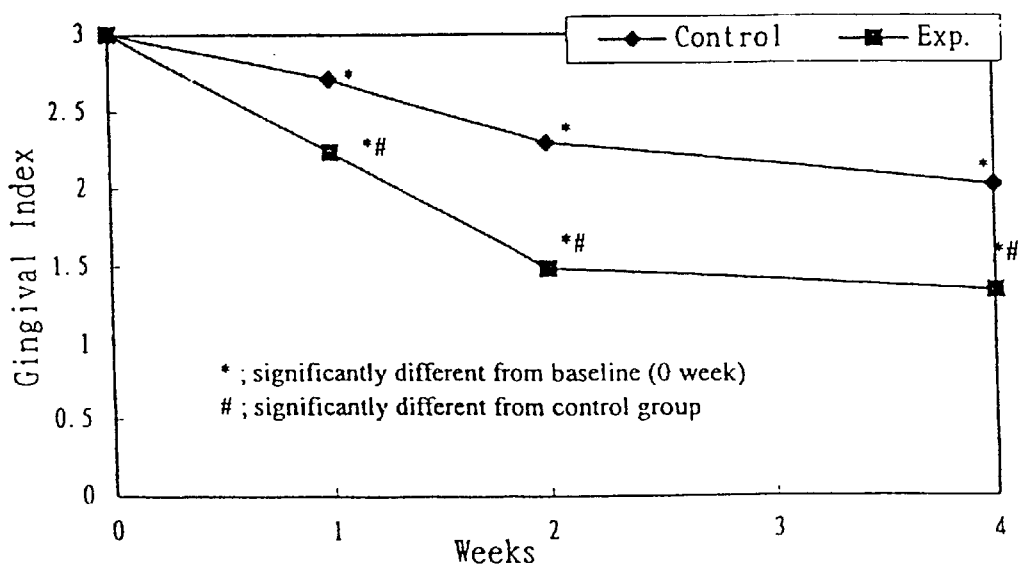
Fig. 2 Gingival Indices

Fig. 3 Pocket Depth
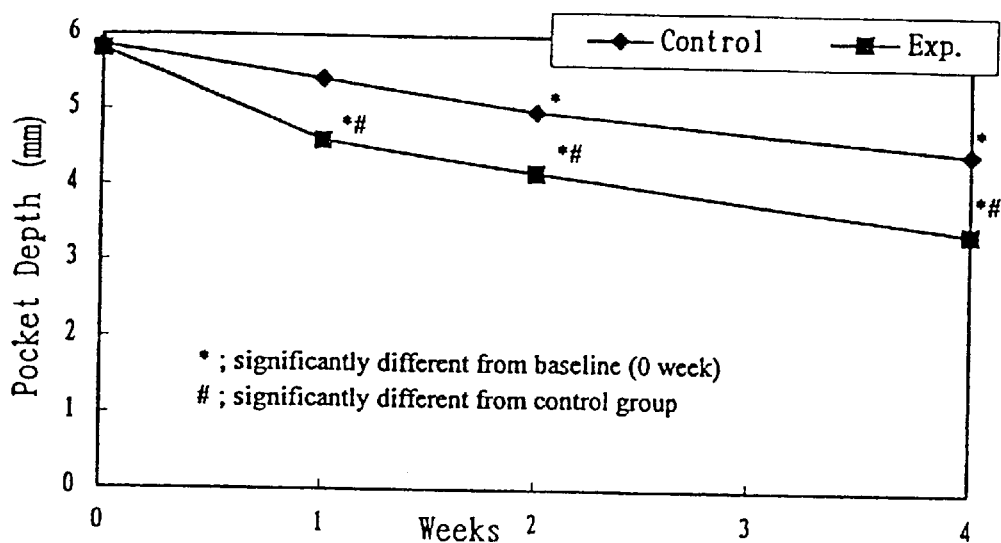
Fig. 4 Bleeding Indices
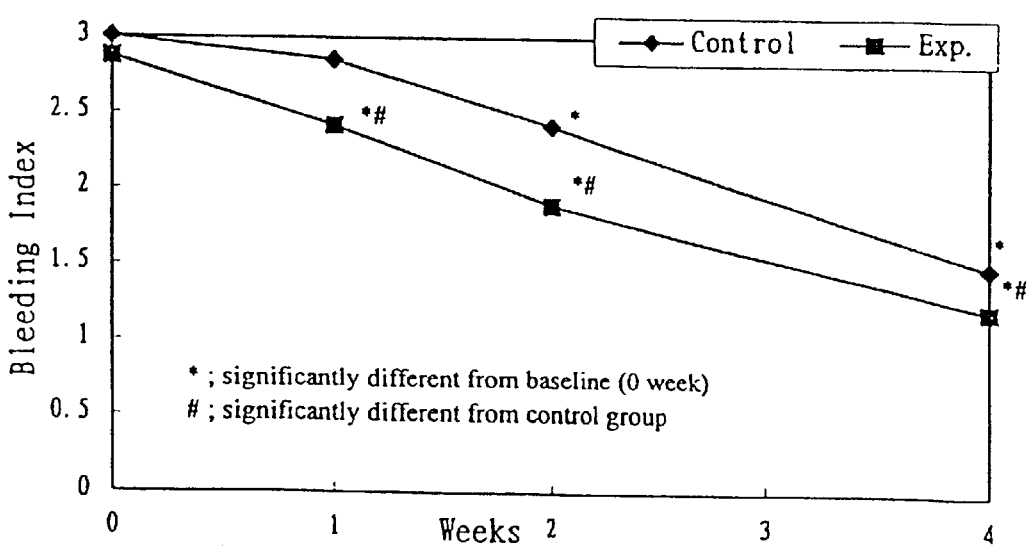

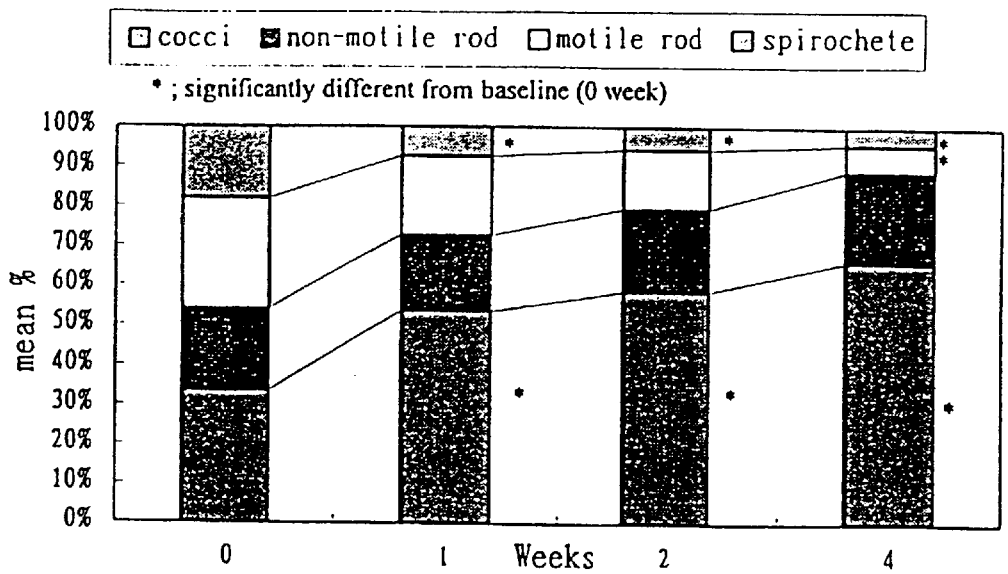
Fig. 5 Control
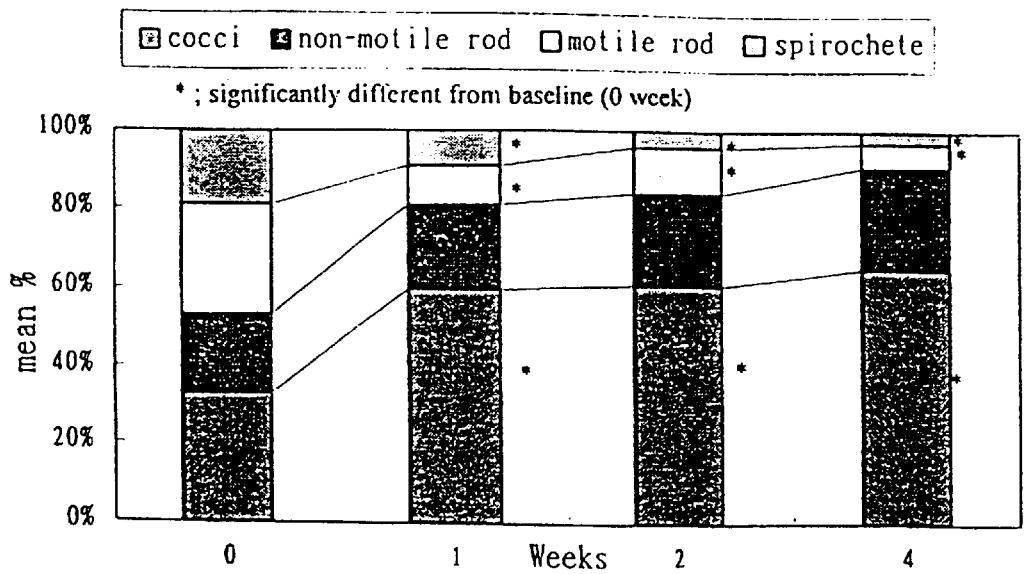
Fig. 6 Experiment

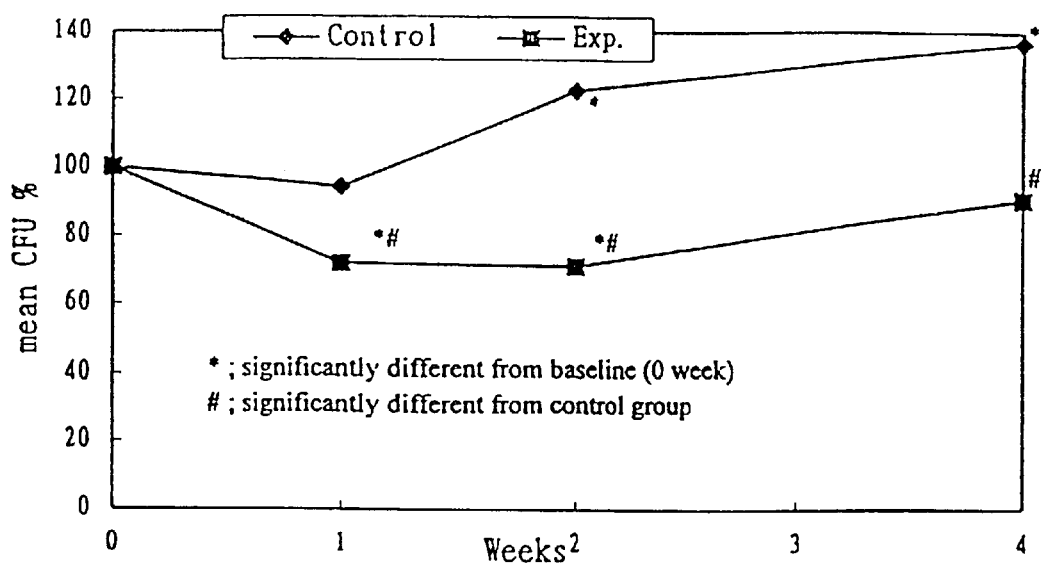
Fig.7 Black-pigmented Bacteroide
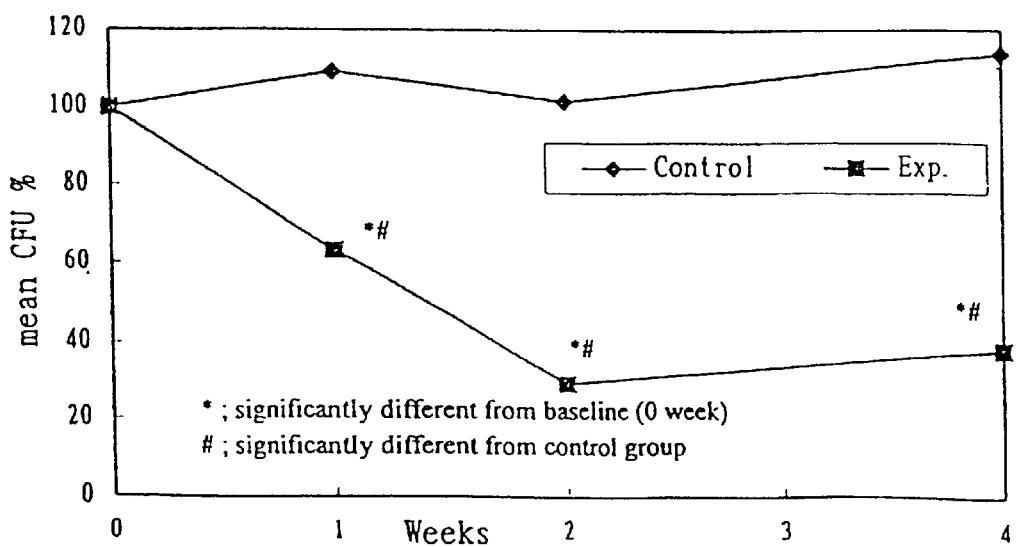
Fig.8 Aerobic blood agar plate

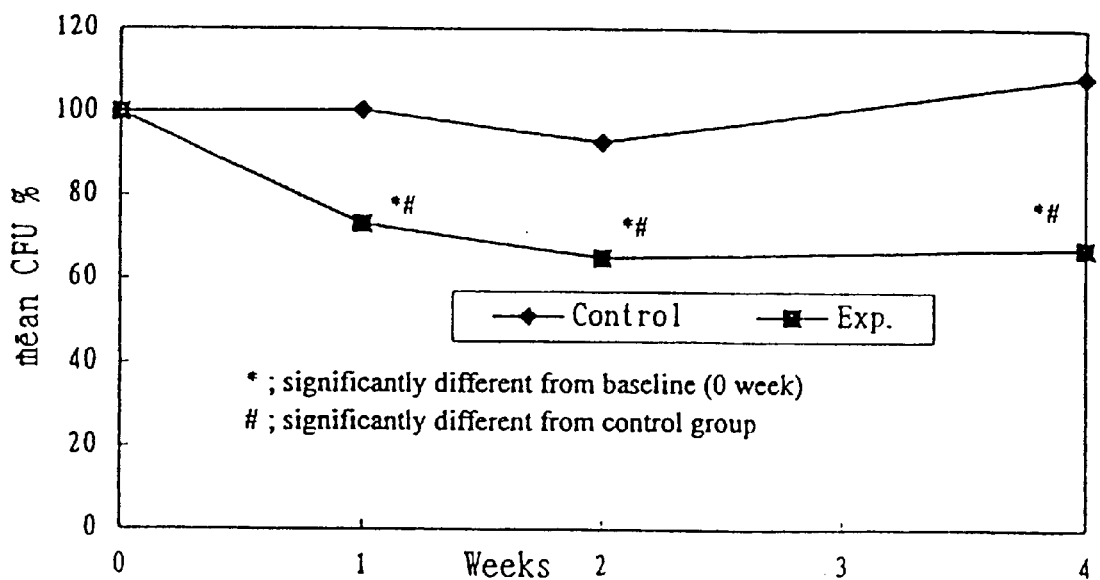

LOCALLY ADMINISTRABLE, BIODEGRADABLE AND SUSTAINED-RELEASE PHARMACEUTICAL COMPOSITION FOR PERIODONTITIS AND PROCESS FOR PREPARATION THEREOF

This application is a 371 of PCT/KR97/00093 filed May 22, 1997.

BACKGROUND OF THE INVENTION

This invention relates to locally administrable, biodegradable and sustained-release pharmaceutical compositions for periodontitis, and its process for preparation thereof, which can show continuous drug effect for a long time by controlling the release time and by making the drug remain in the periodontal pocket for a prolonged time wherein they are prepared by i) making a microsphere containing the physiologically active substance, ii) making a mixture of the microspheres and water-soluble polymer such as polysaccharides iii) making the mixture into the form of film or strip or/and iv) coating the film or strip with aqueous solution of cation such as calcium and barium chlorides.

Periodontitis is an inflammation of the teeth supporting tissue caused by bacterial toxin, which is a metabolizing product of oral bacteria. If periodontitis in the initial stage that is gingivitis is not treated properly, it will develop into severe periodontitis with swelling gingiva, bleeding and bad breath. If periodontitis goes on, the collagen supporting the periodontal membrane is destroyed, and alveolar bone under the teeth is resolved. As a result, periodontal ligament is separated, and a periodontal pocket is formed, and in severe cases, it will develop into advanced periodontal disease which can lead to loss of teeth. Most of the germs causing periodontitis are anaerobic gram-negative bacteria, and they secrete collagenase, which destroy ligament that is connective tissue of the periodontal membrane, and metabolite from above reaction cause periodontitis.

For prevention and treatment of the advanced periodontal disease, removal of the plaque in the periodontal pocket is essential. The methods for removal of the-bacterial plaque can be divided into apparatotherapy and chemotherapy. Apparatotherapies include scaling and root planing, and require the patient's ability to control plaque continuously, but have the disadvantage that apparatotherapies have a limited effect on the part at which it is difficult to brush teeth due to anatomical reason. For supplement of the above disadvantage of apparatotherapies, the plaque control using chemotherapies has been studied and it is reported that chemotherapies are very effective on the removal of bacteria which live in the deep part where instruments are difficult to reach.

The most important thing in the clinical use is to retain the effective concentration of the active substance which control plaque in the bacterial invasion site for a long time without side-effect. The examples of chemical method include irrigating the invaded region with an antibiotic solution, and administering antibiotics systemically. It is known that local administration of antibiotics has a limited effect on the removal of the bacteria causing periodontal disease because antibiotics cannot reach the deep part of the subgingival area or cannot last for enough time. It is reported that the systemic administration is effective on the treatment for the periodontal disease, but in the case of the systemic administration in order to maintain the effective concentration at the infected region it is required that a large dosage of medicine is administered and subsequently side effects result, for example, the appearance of resistant bacteria and undesired action to intestinal bacteria. Therefore, to overcome this defect, the research for the direct administration into the periodontal pocket has been conducted, and it is reported that if tetracycline is administrated locally, only 1/1000 dosage of the systemic administration can bring the same effect (Goodson, J. M. et al., *J. Periodontol*, 56 265–272, 1985).

In order to bring the maximum effect and minimum side-effect, it has been attempted to develop the local drug delivery system using the controlled release system of physiologically active substances such as antibiotics.

There are a few problems that must be solved to treat the periodontitis by a local drug delivery system.

First, a carrier is necessary to transport a physiologically active substance such as antibiotics to the periodontal pocket. A large number of carriers developed so far are substances not absorbed biologically, which must be removed after the drug is released completely and if not, they irritate the periodontal tissue and inhibit the regeneration of the periodontal tissue.

According to U.S. Pat. No. 5,599,553, it is reported that a pharmaceutical preparation composed of minocycline HCl and polycaprolactone in the form of strip can release the active substance for 7 days in the periodontal pocket. In this case polycaprolactone must be removed after the drug is released completely because it takes too long a time to be decomposed in the body.

Second, to treat the periodontitis, effective concentration of the active substance in the periodontal pocket must be maintained for a long time. It is reported that to treat the periodontitis the effective concentration of antibiotics such as monocycline HCl must be maintained for at least 7 to 10 days (Lawter J. R. et al., *Int. sym. cont. Rel, Bioact. Mater.*, 230–31, 1990). It is reported that the therapeutic agent should be retained as long as possible because dental disease is generally chronic (Friedman M. et al., *Pharmaceutical Research*, Vol. 7, No. 4, 313–317, 1990). In addition, it is known that, if administered orally, administration for more than two weeks is effective for the treatment for periodontitis (Lilijenberg B et al., *J. Clin. periodontol.*, 7, 48–61, 1980).

According to U.S. Pat. No. 4,933,182, a pharmaceutical preparation wherein polymeric microparticles containing one or more substances is dispersed into the continuous phase of water soluble polymer. This has an advantage that it can release substance in an independent pattern and it does not give an unpleasant feeling to the patients, but it has disadvantage that administration should be made often because the release of substance is completed in about 6 hours.

Third, it is needed that the process of administration is convenient and quantitative on the basis of the amount of active substance.

According to U.S. Pat. No. 4,175,326, a pharmaceutical preparation containing the active substance in a hollow fiber device made up of cellulose acetate is reported. In order to administer this preparation into the periodontal pocket, fiber should be cut into the length for the dosage, and then the cut fiber must be coiled around the teeth, and then it must be administered in the way of pushing it into the periodontal pocket. This method has disadvantage that it is inconvenient to administer drug into the periodontal pocket quantitatively.

According to WO A1 92/07555 and U.S. Pat. No. 5,324,520, an in situ gel has been reported which is in a liquid state before administration and becomes a little hardened state after administration. Because the formulations are in a liquid state before administration, a special administering tool is needed in the form of a syringe and these formulations also have disadvantage that it is inconvenient to administer quantitatively.

In order to satisfy the most important things for treating the periodontitis, that is to say, biodegradation and continuous drug release, microspheres made up of biodegradable polymer has been provided which is dissolved when it is administered into the periodontal pocket and releases drug continuously. For example, it is reported that they suspended PLGA microspheres including tetracycline in Pluronic F 127 gel and then inserted the prepared formulation in the periodontal pocket (EP A1 244118). In addition, it is reported that they can maintain the effective concentration in the periodontal pocket for 14 days by inserting microsphere containing minocycline and PLGA (Lawter J. R. et al., *Int. Symp. Cont. Rel. Bioact. Mater.*, 230–231, 1990), and filed a patent application therefor. The formulation for treating periodontitis using such biodegradable microspheres can retain the effective drug concentration in the periodontal pocket for a long time by single dose, and the feeling of foreign substance does not exist because the formulation was prepared by microparticle, and there is no need to remove after treatment because the formulation is biodegradable. However, since microspheres prepared in the form of gel can not last for a long time due to its hydrolytic property, there is inconvenience that it should be prepared just before use, and that a special administering tool is needed in order to insert gel into the periodontal pocket. And it is difficult to administer quantitatively and accurately when we insert the microspheres directly into the periodontal pocket.

Therefore, in order to develop ideal formulations for periodontitis, it is desirable that a biodegradable substance is used to control drug release, the effective drug concentration is maintained continuously and the administration is convenient for patients.

The present inventors have been conducted the continuous study for the ideal formulation for periodontitis, and we found that if the biodegradable microspheres containing physiologically active substance for periodontitis is mixed with the hydrogel of water soluble polymer and then the mixture is made into the form of thin film or strip, and this film or strip is inserted into the periodontal pocket, it will show the continuous effect for a long time, since water soluble polymer is decomposed slowly, on contacting saliva and the gingival crevice fluid, and subsequently only the microspheres became left alone in the periodontal pocket and these microspheres release the active substance continuously. In addition, the inventors discovered that when the film or strip is spray-coated with aqueous solution of cation salt such as $Ca^{2+}$ or $Ba^{2+}$, disintegration time can be controlled effectively.

SUMMARY OF THE INVENTION

The present invention relates to the locally administrable, biodegradable, and sustained-release pharmaceutical compositions and process for preparation thereof.

More specifically, the present invention provides composition in the form of thin film or strip composed of microspheres made with biodegradable polymer and water-soluble polymer such as polysaccharides.

And the present invention provides a composition composed of the above thin film or strip coated with cation salt aqueous solution.

In addition, the present invention provides a process for preparing a composition comprising the steps, 1) making the biodegradable microspheres containing the biologically active substance, 2) mixing the microsphere and water-soluble polymer such as polysaccharides, 3) making the mixture into the form of thin film or strip. The present invention provides process for preparing composition-comprising the step of coating the film or strip with metal cation aqueous solution in addition to the above-mentioned process.

BRIEF DESCRIPTION OF THE DRAWINGS

In the accompanying figures:

FIG. 1 is indices of plaque comparing control group with those of experimental group;

FIG. 2 is indices of gingiva comparing control group with those of experimental group;

FIG. 3 is pocket depth comparing control group with those of experimental group;

FIG. 4 is indices of bleeding comparing control group with those of experimental group;

FIG. 5 represents the variation of ratio of cocci, non-motile rod, motile rod and spirochete in the control group;

FIG. 6 represents the variation of ratio of cocci, non-motile rod, motile rod and spirochete in the experimental group;

FIG. 7 is CFU of black-pigmented bacteroide in control vs experimental group;

FIG. 8 is CFU in control vs experimental group cultured on aerobic blood agar plate;

FIG. 9 is CFU in control vs experimental group cultured on anaerobic blood agar plate;

DETAILED DESCRIPTION OF THE INVENTION

The physiologically active substance of the present invention which can be used for treating periodontitis contains antibiotics, local anesthetics antiinflammatory analgesics, and steroid hormones. Antibiotics which can be used in the present invention contain ampicillin, amoxicillin, erythromycin, tetracycline, minocycline, oxytetracycline, doxycycline, metronidazol, bacitracin, kitasamycin, spiramycin, ornidazole, and salts thereof, which are used generally to treat periodontitis, and local anesthetics which can be used in the present invention contain lidocaine, procaine, dibucaine, and benzocaine, antiinflammatory analgesics which can be used in the present invention contain diclofenac, flubiprofen, ibuprofen, ketoprofen, aspirin, mefenamic acid and acetaminophen, and steroid hormones which can be used in the present invention contain dexamethasone, triamcinolone acetonide, hydrocortisone and epihydrocortisone.

Biodegradable polymers used in preparing the microsphere of the present invention are polymers of the derivatives of α-hydroxy-carboxylic acid, for example, polymers of glycolic acid(PGA), polymers of lactic acid(PLA), and copolymers of lactic acid and glycolic acid(PLGA) which can be hydrolyzed into water and carbon dioxide which are not harmful to human body.

The molecular weight of these polymers have an important effect on the period of drug release and degradation of the microspheres.

When we use a polymer group of PLA, PGA and PLGA, the more the molecular weight increases, the longer the drug release time as well as degradation of the polymers occurs. The release time and degradation of the polymers is postponed when the ratio of lactic acid increased in the use of PLGA copolymer.

If we make use of this property, we can control the releasing time of microspheres. Therefore when the releasing time is determined as two weeks to treat periodontitis, the desirable range of molecular weight is 4,000 to 50,000, and the more desirable range is 5,000 to 15,000. In order to administer the various kinds of drugs simultaneously, we can make microspheres using polymers of different molecular weight, and each microspere will show the independent release pattern.

The inventors invented a pharmaceutical composition in the form of film or strip made up of the mixture of the microspheres and wafer-soluble polymer hydrogel in order to administer an active substance quantitatively into the periodontal pocket. In other words, if the microspheres can be maintained in their original form in the film or strip made up of the mixture of microspheres and water-soluble polymer, the quantity of the microsphere in the film or strip can be calculated and the quantity of administered drug into the periodontal pocket can be determined by the mixture ratio of the microspheres and water-soluble polymer, and quantitative administration can be possible.

The desirable water-soluble polymer used in the pharmaceutical composition of the present invention should be harmless to human body and viscous in the aqueous solution, and easy to be formed into the film or strip after drying. These contain the polysaccharides such as pectin, carrageenan, gelan, sodium alginate or chitosan.

In the present invention, if we coat the above-mentioned film or strip with the aqueous solution of cation such as calcium and barium, it is possible to delay the disintegrating time.

That is, if film or strip without coating is administered into the periodontal pocket, it swells so feast on contacting with saliva or gingival crevice fluid that a part of the film or strip can be cut of the periodontal pocket, and there is a large opportunity to lose the part of the film or strip, and to decrease the amount of an active substance in the periodontal pocket, and we can not have a desirable treatment effect, because the dosage is practically diminished with respect to the amount delivered to the periodontal pocket. To solve this problem, the present inventors invented the pharmaceutical composition using a complex of the polysaccharides and metal ion.

When water-soluble polymer such as polysaccharides forms complex with the metal ion, its solubility to the water decreases and the rate of the swelling gets slow. Therefore, in the early stage of the administration, the possibility of the loss of the film or strip disappears, and the administered drug remains in the periodontal pocket more safely.

Since the solubility to the water and swelling rate of the complex make up of the polysaccharides and metal depend on the kinds of the metal cation, we can choose a proper metal ion considering the treatment period, etc.

The desirable cation salt may contain cation chlorides, such as calcium chloride, magnesium chloride, barium chloride, and aluminum chloride.

Especially calcium chloride is suitable to the formulation which is hydrated by saliva or gingival crevice fluid in the short time, 3 to 6 hrs, and barium chloride is suitable to the pharmaceutical formulation for longer time, one week to two weeks.

It is possible to make film or strip coated with cation aqueous solution utilizing a simple step such as spray-coating when we use polysaccharides.

It is found that different formulations have their has own disintegration time. The formulation which is not combined with metal ion maintains its original shape in the periodontal pocket only for two hours, calcium-polysaccharides for 3 to 6 hrs, and barium-polysaccharides for more than one week. When the formulation is disintegrated, only the microspheres remain in the periodontal pocket, and release an active substance continuously.

Therefore, in the present invention it is possible to administer an active substance into the periodontal pocket quantitatively by using film or strip made up of polysaccharides and microspheres, and it is possible to control the maintenance of the film or strip in the periodontal pocket by controlling the disintegration time by coating the film or strip with aqueous solution of cation salt.

The following explains the process for preparing the locally administrable, biodegradable and sustained-release pharmaceutical composition for periodontitis, 1) the step of making microspheres, by dissolving a biodegradable polymer such as PLA or PLGA in methylene chloride, by suspending a finely-powdered active substance, and by emulsifying the suspended solution in an aqueous solution containing a surfactant, 2) the step of making hydrogel, by mixing microspheres and polysaccharides and by adding distilled water, 3) the step of foming into film or strip.

In addition, another process for preparing locally administrable, biodegradable and sustained-release pharmaceutical composition includes step 4) for coating the film or strip with aqueous solution of cation salt in addition to the above-mentioned step i.), step 2), and step 3).

The process for preparing the locally administrable, biodegradable pharmaceutical composition for periodontitis will be explained by steps in detail in the following.

I. Step 1

The microspheres used in the present invention are prepared by the process which is in applied for patent by the present inventors' Korean patent No. 95-10671, on which the priority of the present invention is based.

Microspheres which contain more than 20 weight % of an active substance and release the active substance at the effective concentration and within 2 weeks are made as the following.

First of all, in the case that an active substance is water-soluble, we crushed the substance into the average diameter below 5 $\mu$m by using a Jet-mill. In the case of organic-soluble substances, this process is not necessary.

We mixed biodegradable polymer, PLA or PLGA, with the active substance in the proper ratio, addition of methylene chloride into it, and the mixutre is mixed well, followed by cooling down below 20° C.

After emulsifying the polymer solution by addition to aqueous polyvinyl alcohol was precooled below 5° C., the emulsion is diluted with distilled water. Finally, methylene chloride is evaporated to achieve our goal was mentioned above. When we made microspheres according to the above method using D, L-PLA whose molecular weight is 6,500 to 8,000, the release of active substance was completed within 2 weeks.

When we used PLGA whose molecular weight is 8,000 to 10,000 the release of substance was accomplished within 2 weeks also. The desirable amount of active substance contained in the microspheres is about 10 to 30 weight %. Especially 20 to 25 weight % is more desirable.

In addition, the particle size of microspheres have important effect on the drug content and the rate of the drug release. The average particle size which can be used is 1 to 500 μm, and 10 to 200 μm is desirable, and 20 to 150 μm is more desirable.

It is desirable that the microspheres release the active substance continuously for more than 7 days and less than 20 days.

II. Step 2

The process for mixing polysaccharide and microspheres will be explained in the following.

First of all, we mixed sustained-release microspheres containing the active substance and polysaccharides. At this time the mixing ratio is the important factor not only on the administration volume of the formulation, but also on the extent of loss of microspheres from the periodontal pocket due to increased volume as polysaccharide is swollen. Therefore, it is desirable to use polysaccharide as little as possible, and it is desirable that the ratio of polysaccharide to the total mixed pharmaceutical composition is 5 to 50 weight %, and more desirable is 5 to 30 weight %.

Then we added distilled water to the above mixture and made hydrogel of polysaccharide in which microspherses are suspended. The concentration of polysaccharide, that is, the quantity of the added distilled a very important factor, when we make film or strip. If the quantity of the added distilled water is too large, it is difficult to form film or strip, and if the quantity of the added distilled water is too small, it is difficult to make film or strip containing an active substance homogeneously because it is difficult to disperse microspheres in the hydrogel evenly. Thus, considering the above factors, it is desirable to add the distilled water enough to make hydrogel which contains polysaccharide below 50 weight %, and it is more desirable to make hydrogel which contains polysaccharide at the ratio of 1 to 20 weight %.

III. Step 3

In order to insert the above hydrogel into the periodontal pocket, it is formed into the film or strip as the following.

First, hydrogel is put and flattened on an acryl board or metal board, and then covered with a polyester film coated with silicon, and compressed with a roller to even the thickness, and then polyester film is removed, and dried in the air. The resultant film is cut into the proper size to insert it into periodontal pocket. We can make strip by another method wherein the above water-soluble polymer hydrogel is put in a frame and compressed. On making film or strip, we determine the thickness of the film or strip considering the size of the periodontal pocket. The desirable thickness of the film or strip is below 2 mm, and the more desirable thickness is 0.1 to 1.0 mm. The desirable example of the pharmaceutical composition is 6 mm–2 mm in width and 0.1 to 2 mm in thickness are wedge type in the shape.

IV. Step 4

To increase the maintenance of the formulation in the periodontal pocket, it is desirable to decrease the viscosity after hydration and to the disintegration time by coating film or strip with aqueous solution of cation salt. The desirable cation salt contains calcium chloride, magnesium chloride, barium chloride and aluminum chloride, and especially calcium chloride is suitable to the pharmaceutical composition of the present invention which is hydrated by saliva or gigival crevice fluid in 3 to 6 hrs, and barium chloride is suitable to the compositions which can be maintained for 1 to 2 weeks.

The desirable concentration of 2(II) or 3(III) cation aqueous solution is 1 to 10%, and 2 to 5% is more desirable.

There are two kinds of coating methods. One is to coat film or strip by soaking it in aqueous solution of cation and the other is to coat the film or strip by spraying the aqueous solution of cation. The latter is more desirable.

The pharmaceutical composition for periodontitis of the present invention is inserted into the periodontal pocket, and polysaccharide is hydrated by saliva and dissolved, and only the biodegradable microspheres remain in the periodontal pocket and release the active substance for 1 to 2 weeks.

Because the present invention is for local administration, we formulate with the minimum dosage for the periodontal pocket. Consequently one can minimize the side effect which can be accompanied when one administers an excess amount for extended time.

And because the pharmaceutical composition contains sustained-release microsphere, administering effect of single dose can last for two weeks. In addition, because the form of pharmaceuticalcomposition is film or strip, we can administer the drug with forceps conveniently, and because the composition consists of biodegradable substance, there is no need to remove the remnant after the release of an active substance is completed.

And by coating the drug with 2(II) cation chloride aqueous solution, the pharmaceutical composition of the present invention can remain in the periodontal pocket more safely.

Therefore, it has great advantage that we can maximize the drug release effect and the usage is very convenient. The present invention will be explained in more detail by examples.

The following examples are only for showing the application of the present invention, but the claims of the present invention is not limited within these examples.

Preparation example 1

The preparation of the biodegradable microsphere containing antibiotics

Minocycline loaded microspheres were prepared by a modified O/W emulsion technique. A 0.6 g of micronized minocycline HCl (particle size was below 5 μm) was added to 2 ml methylene chloride containing 1.4 g polylactic acid of molecular weight 7,500. The relultant suspension was poured into a beaker containing 200 ml of 5% polyvinyl alcohol aqueous solution at 5° C. that was being mechanically stirred. Stirring continued for 1 hr to permit evaporation of the solvent. The microspheres were collected, washed with water, and lyophilized using a freeze-dryer. The average particle size was 100 μm and the drug content was 24 weight %.

Preparation example 2 to preparation example 7

We prepared microspheres by the same method as described in preparation example 1 using various polymers and active substances. Table 1 shows their particle size and content of the active substances.

TABLE 1

| | Microspheres containing active substance. | | | |
|---|---|---|---|---|
| | polymer (average molecular weight) | active substance | Average size (μm) | drug content (weight %) |
| preparation example 2 | PLA(8,000) | Minocycline HCl | 120 | 22 |
| preparation example 3 | PLA(10,000) | Tetracycline HCl | 75 | 20 |
| preparation example 4 | PLGA(8,500) | Minocycline HCl | 100 | 23 |

TABLE 1-continued

Microspheres containing active substance.

| | polymer (average molecular weight) | active substance | Average size (μm) | drug content (weight %) |
|---|---|---|---|---|
| preparation example 5 | PLA(14,000) | Metronidazole | 110 | 25 |
| preparation example 6 | PLGA(8,500) | Flubiprofen | 100 | 27 |
| preparation example 7 | PLA(7,500) | Dibucaine | 120 | 21 |

EXAMPLE 1

The preparation of the pectin film containing microspheres

After we mixed 0. g of microsphere prepared in preparation example 1 and 0.2 g of pectin, 2.0 g of distilled water is added to the mixture to obtain the hydrogel containing microspheres.

The above hydrogel is put and flattened into an acrylic mold box whose width is 10 cm–O10 nm, and whose thickness is 0.5 mm, and whose bottom is closed. And we with polyester film coated with silicon, and compressed it by roller, and removed the polyester film and dried at the room temperature. The resultant. film is cut in the size of 6mm–O2 mm.

EXAMPLE 2

The preparation of pectin strip containing microspheres

After we prepared hydrogel containing microspheres by the same method as described in example 1 we put it into the wedge type mold whose width is 6 mm, and whose length is 2 mm and whose depth is 0.1 mm to 0.5 mm. And covered polyester film coated with silicon, and compressed it by roller, and removed the polyester film, and dried it at the room temperature, and separated strip from the mold.

EXAMPLE 3

The preparation of the sodium alginate film containing microspheres

After we mixed a 0.1 g of sodium alginate and 0.85 g of microsphere of the above preparation example 2, we added 1.5 g of distilled water to the mixture to obtain the hydrogel containing microspheres. We prepared film with hydrogel by using the same method as described in example 1.

EXAMPLE 4

The preparation of the calcium alginate film containing microspheres

The calcium alginate film is prepared by spraying 2% calcium chloride aqueous solution to the sodium alginate film prepared in Example 3 and drying it.

EXAMPLE 5 to EXAMPLE 16

The strip or film was prepared by the same method as described in example 1 to 4 by using microspheres which was prepared by the same method as described in preparation example 2 to example 7. The result is shown in table 2.

TABLE 2

The film or strip containing microspheres

| | Microsphere | Polysaccharides | Microspheres/ Polysaccharides | Shape | Coating |
|---|---|---|---|---|---|
| Example 5 | Preparation Example 2 | sodium alginate | 80/20 | Strip | — |
| Example 6 | Preparation Example 3 | sodium alginate | 85/15 | Strip | Calcium Chloride |
| Example 7 | Preparation Example 3 | sodium alginate | 85/15 | Strip | Barium Chloride |
| Example 8 | Preparation Example 4 | pectin | 90/10 | Film | Calcium Chloride |
| Example 9 | Preparation Example 4 | pectin | 90/10 | Film | Barium Chloride |
| Example 10 | Preparation Example 5 | carrageenan | 90/10 | Film | Calcium Chloride |
| Example 11 | Preparation Example 3 | carrageenan | 80/20 | Film | Barium Chloride |
| Example 12 | Preparation Example 4 | carrageenan | 80/20 | Strip | — |
| Example 13 | Preparation Example 4 | gelan | 80/20 | Strip | — |
| Example 14 | Preparation Example 6 | gelan | 70/30 | Film | Calcium Chloride |
| Example 15 | Preparation Example 6 | gelan | 80/20 | Film | Barium Chloride |
| Example 16 | Preparation Example 7 | gelan | 75/25 | Film | Barium Chloride |

Test 1

In vitro release test.

Films or strips of above examples were tested in 10 ml of 10 mM phosphate buffer pH 7.4 at 37° C. in a shaking water bath. The amount of released drug was analyzed by measuring the UV absorbance according to the time. Table 3 shows the results.

TABLE 3

Drug release Test

| | Hour(Day) | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|
| The Cumulating Releasing Quantity | Example 1 | 20 | 30 | 39 | 47 | 55 | 61 | 69 | 77 | 84 | 90 | 94 | 97 | 99 | 100 | — | — |
| | Example 3 | 18 | 25 | 33 | 42 | 48 | 56 | 63 | 70 | 76 | 80 | 85 | 89 | 93 | 95 | 97 | 99 |
| | Example 4 | 19 | 26 | 34 | 43 | 49 | 57 | 64 | 70 | 76 | 81 | 86 | 89 | 93 | 95 | 98 | 100 |
| | Example 6 | 22 | 28 | 34 | 40 | 46 | 52 | 59 | 65 | 71 | 77 | 83 | 88 | 92 | 95 | 97 | 99 |
| | Example 7 | 21 | 27 | 33 | 39 | 45 | 51 | 57 | 63 | 69 | 75 | 80 | 85 | 90 | 94 | 97 | 99 |
| | Example 8 | 16 | 25 | 34 | 42 | 50 | 58 | 66 | 74 | 81 | 88 | 94 | 98 | 100 | — | — | — |
| | Example 11 | 22 | 28 | 34 | 40 | 46 | 52 | 58 | 64 | 70 | 76 | 82 | 87 | 91 | 94 | 97 | 100 |
| | Example 12 | 17 | 26 | 35 | 433 | 51 | 58 | 66 | 74 | 80 | 87 | 93 | 97 | 100 | — | — | — |
| | Example 13 | 18 | 28 | 34 | 42 | 502 | 58 | 66 | 74 | 80 | 87 | 93 | 97 | 100 | — | — | — |
| | Example 14 | 20 | 28 | 36 | 44 | 52 | 60 | 67 | 75 | 82 | 89 | 96 | 99 | 100 | — | — | — |
| | Example 15 | 20 | 28 | 36 | 44 | 52 | 60 | 67 | 75 | 82 | 89 | 96 | 99 | 100 | — | — | — |
| | Example 16 | 21 | 28 | 36 | 44 | 52 | 60 | 67 | 75 | 82 | 89 | 94 | 97 | 99 | 100 | — | — |

Test 2
Disintegration test of the pharmaceutical composition

Among the above examples, we added the drug prepared by sodium alginate or pectin, and the drug coated with calcium chloride aqueous solution on this drug, and the drug coated with barium chloride aqueous solution on this drug to the pH 7.4 phosphate buffer solution at 37° C., and measured the time in which the formulation disintegrated completely. The result is in table 4.

TABLE 4

The Result of dissolution test of the drug.

| Sample | Polysaccharides | Coating | Time necessary for the dissolution of the drug |
|---|---|---|---|
| Example 3 | sodium alginate | — | 1 hr |
| Example 6 | sodium alginate | $Ca^{2+}$ | 4 hr |
| Example 7 | sodium alginate | $Ba^{2+}$ | 11 days |
| Example 1 | pectin | — | 1.5 hr |
| Example 8 | pectin | $Ca^{2+}$ | 5 hr |
| Example 9 | pectin | $Ba^{2+}$ | 12 days |

Test 3
Drug effect test administrated to the animal

This test was conducted in order to confirm a physiological effect of the pharmaceutical composition for the periodontitis (composition composed of sodium alginate and polylactic acid microspheres containing minocycline) prepared by the method described in Example 3.

The above formulations (film cut by 6×2 mm) were administered to the periodontal pockets of dogs, and after 0, 1, 2, and 4 weeks, each clinical index was measured. The morphology of bacteria was measured with a microscope, and the colony number of bacteria by cultivation was measured.

And the data like this was analyzed statistically by ANOVA method in order to confirm the significant difference between before administration and after administration.

The clinical indices such as plaque indices, gingival indices, and bleeding indices were measured by Loe & Silness method, and the depth of periodontal pocket was measured with William's probe. Regarding to the morphology of bacteria, proportion of cocci, non-motile rod, motile rod and spirochete was measured with a microscope for each week. Regarding to cultivation of microorganisms, the variation ratio dependent upon time was measured for each week. And the following result was obtained.

1. Clinical indices such as plaque indices, gingival indices, the depth of periodontal pocket and bleeding indices showed significant difference after administration compared to a control group(Table 5–8, FIG. 1–4).

2. After administration, the ratio of cocci and non-motile rod was increased, and motile rod and spirochete were reduced (Table 9–12, FIG. 5–6).

3. Colony Forming Unit (CFU) of each media was significantly reduced when bacteria was cultivated in aerobic or anaerobic blood agar media(Table 13–15, FIG. 7–9).

According to a result of the above test, it is proved that the clinical indices, the variation of bacteria and the concentration of drug In the periodontal pocket shows that the pharmaceutical composition for periodontitis of the present invention is very effective for longer than 2 weeks, when it is locally administered.

TABLE 5

Comparison of plaque indices

| | group | |
|---|---|---|
| week | Control | Experiment |
| 0 | 3.00 ± 0.00 | 3.00 ± 0.00 |
| 1 | 3.00 ± 0.00 | 2.71 ± 0.46*# |
| 2 | 2.42 ± 0.50* | 1.47 ± 0.60*# |
| 4 | 1.66 ± 0.48* | 1.33 ± 0.48*# |

Note
*Significantly different from baseline (0 week)
Significantly different from control group

TABLE 6

Comparison of gingival indices

| | group | |
|---|---|---|
| week | Control | Experiment |
| 0 | 3.00 ± 0.00 | 3.00 ± 0.00 |
| 1 | 2.71 ± 0.46* | 2.23 ± 0.43*# |
| 2 | 2.28 ± 0.46* | 1.47 ± 0.51*# |
| 4 | 2.00 ± 0.59* | 1.33 ± 0.48*# |

Note
*Significantly different from baseline (0 week)
Significantly different from control group

TABLE 7

Comparison of pocket depth

| week | group | |
|---|---|---|
| | Control | Experiment |
| 0 | 5.85 ± 1.15 | 5.80 ± 1.12 |
| 1 | 5.42 ± 1.43 | 4.61 ± 0.58*# |
| 2 | 5.00 ± 0.00* | 4.19 ± 0.67*# |
| 4 | 4.50 ± 0.78* | 3.44 ± 0.85*# |

Note
*Significantly different from baseline (0 week)
Significantly different from control group

TABLE 8

Comparison of bleeding indices

| week | group | |
|---|---|---|
| | Control | Experiment |
| 0 | 3.00 ± 0.00 | 2.87 ± 0.32 |
| 1 | 2.85 ± 0.35 | 2.42 ± 0.50*# |
| 2 | 2.42 ± 0.50* | 1.90 ± 0.43*# |
| 4 | 1.50 ± 0.51* | 1.22 ± 0.42*# |

Note
*Significantly different from baseline (0 week)
Significantly different from control group

TABLE 9

Proportion of cocci to total microorganisms for each week (particular bacteria/total bacteria × 100, mean % ± SD)

| week | group | |
|---|---|---|
| | Control | Experiment |
| 0 | 33.51 ± 11.86 | 32.92 ± 9.14 |
| 1 | 54.49 ± 12.08* | 59.25 ± 12.14* |
| 2 | 60.76 ± 9.81* | 60.11 ± 11.62* |
| 4 | 66.35 ± 8.42* | 65.01 ± 10.07* |

Note
*Significantly different from baseline (0 week)

TABLE 10

Proportion of non-motile rod to total microorganism for each week (mean % ± SD)

| week | group | |
|---|---|---|
| | Control | Experiment |
| 0 | 20.47 ± 4.33 | 20.00 ± 6.41 |
| 1 | 19.65 ± 8.75 | 21.45 ± 9.13 |
| 2 | 21.68 ± 8.93 | 23.20 ± 11.24 |
| 4 | 22.96 ± 9.61 | 25.68 ± 9.90 |

Note
*Significantly different from baseline (0 week)

TABLE 11

Proportion of motile rod to total microorganism for each week (mean % ± SD)

| week | group | |
|---|---|---|
| | Control | Experiment |
| 0 | 27.99 ± 6.49 | 28.02 ± 6.43 |
| 1 | 20.01 ± 5.28 | 10.11 ± 7.01* |
| 2 | 15.21 ± 8.90 | 11.87 ± 7.03* |
| 4 | 6.61 ± 4.11* | 6.20 ± 4.43* |

Note
*Significantly different from baseline (0 week)

TABLE 12

Proportion of spirochete to total microorganism for each week (mean % ± SD)

| week | group | |
|---|---|---|
| | Control | Experiment |
| 0 | 17.94 ± 8.12 | 19.05 ± 7.19 |
| 1 | 7.51 ± 7.20* | 9.16 ± 5.37* |
| 2 | 5.86 ± 6.46* | 4.25 ± 3.77* |
| 4 | 4.32 ± 2.60* | 3.13 ± 3.19* |

Note
*Significantly different from baseline (0 week)

TABLE 13

Comparison of Black-pigmented Bacteroide (mean CFU % ± SD)

| week | group | |
|---|---|---|
| | Control | Experiment |
| 0 | 100.00 ± 0.00 | 100.00 ± 0.00 |
| 1 | 94.31 ± 37.08 | 71.80 ± 16.53*# |
| 2 | 122.30 ± 48.34* | 71.07 ± 24.50*# |
| 4 | 136.72 ± 38.04* | 90.98 ± 26.02# |

Note
*Significantly different from baseline (0 week)
Significantly different from control

TABLE 14

Comparison of aerobic blood agar plate (mean CFU % ± SD)

| week | group | |
|---|---|---|
| | Control | Experiment |
| 0 | 100.00 ± 0.00 | 100.00 ± 0.00 |
| 1 | 109.21 ± 13.64 | 63.31 ± 43.11*# |
| 2 | 101.41 ± 19.48 | 29.18 ± 17.91*# |
| 4 | 113.72 ± 23.66 | 38.34 ± 18.69# |

Note
*Significantly different from baseline (0 week)
Significantly different from control

TABLE 15

Comparison of Anaerobic blood agar plate
(mean CFU % ± SD)

| | group | |
|---|---|---|
| week | Control | Experiment |
| 0 | 100.00 ± 0.00 | 100.00 ± 0.00 |
| 1 | 100.40 ± 20.34 | 73.17 ± 6.84*# |
| 2 | 92.85 ± 13.13 | 65.12 ± 15.17*# |
| 4 | 108.41 ± 13.47 | 67.48 ± 16.65# |

Note
*Significantly different from baseline (0 week)
Significantly different from control

What is claimed is:

1. A locally administrable, biodegradable and sustained-release delivery system for treatment of periodontitis comprising:
   A) microspheres releasing therapeutically active substances for treating periodontitis which comprises:
      1) active substance in an amount of more than 20 weight % of the microsphere,
      2) biodegradable polymer selected from the group consisting of polylactic acid and poly(lactic-co-glycolic) acid whose weight average molecular weight is in the range of 4,000 to 50,000; and
   B) bivalent metal ion complex of polysaccharides selected from the group consisting of pectin, carrageenan, gellan gum, sodium alginate and chitosan,
   wherein the release of the active substance is determined by said microspheres and is not affected by polysaccharide which is used as a supporter or a binder of the microspheres and has a property of disintegrating slowly in accordance with substituting the complexed bivalent metal ion with monovalent metal ion abundant in body fluid.

2. The locally administrable, biodegradable and sustained-release delivery system according to claim 1, wherein said active substance includes antibiotics selected from the group consisting of amphicilin, amoxicillin, erythromycin, tetracycline, minocycline, oxytetracycline, doxycycline, metronidazol, bacitracin, kitasamycin, spiramycin, ornidazole and their salts.

3. The locally administrable, biodegradable and sustained-release delivery system according to claim 1, wherein said active substance includes local anesthetics selected from the group consisting of lidocaine, procaine, dibucaine and benzocaine.

4. The locally administrable, biodegradable and sustained-release delivery system according to claim 1, wherein said active substance includes antiinflammatory analgesics selected from the group consisting of diclofenac, flubiprofen, ibuprofen, ketoprofen, aspirin, mefenamic acid and acetaminophen.

5. The locally administrable, biodegradable and sustained-release delivery system according to claim 1, wherein said active substance includes steroid hormone selected from the group consisting of dexamethasone, triamcinolone acetonide, hydrocortisone and epihydrocortisone.

6. The locally administrable, biodegradable and sustained-release delivery system according to claim 1, wherein the bivalent metal ion is selected from the group consisting of $Ca^{2+}$, $Mg^{2+}$ and $Ba^{2+}$.

7. A process for the preparation of locally administrable, biodegradable and sustained-release delivery system for periodontitis, comprising the steps of:
   A) making microspheres containing a therapeutically active substance by dissolving biodegradable polymer in a solvent, suspending the active substance ground to 1–5 μm in diameter into the solution, emulsifying the suspended solution wherein polyvinyl alcohol is contained therein in an amount of 1 to 20 weight % to the solution, and evaporating the solvent;
   B) making a hydrogel by mixing the microspheres and polysaccharide in ratio of 95:5 to 50:50, and then adding distilled water to make the final concentration of polysaccharide of 1 to 20 weight % of the hydrogel;
   C) making films or strips from the hydrogel; and
   D) coating and drying by spray-coating onto films or strips with an aqueous solution of bivalent metal ion.

8. The process according to claim 7, wherein the concentration of the bivalent metal ion is 2 to 5 weight % of the solution.

* * * * *